United States Patent
Koppe et al.

(10) Patent No.: US 7,103,135 B2
(45) Date of Patent: Sep. 5, 2006

(54) METHOD AND APPARATUS FOR GENERATING AN IMPROVED IMAGE OF NATURAL TISSUE IN RECONSTRUCTING BODY IMAGES FROM 3D-MEASUREMENTS

(75) Inventors: Reiner Koppe, Hamburg (DE); Johannes Catharina Antonius Op De Beek, Eindhoven (NL); Erhard Paul Artur Klotz, Neumuenster (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/524,422

(22) PCT Filed: Jul. 24, 2003

(86) PCT No.: PCT/IB03/03351

§ 371 (c)(1),
(2), (4) Date: Feb. 14, 2005

(87) PCT Pub. No.: WO2004/017263

PCT Pub. Date: Feb. 26, 2004

(65) Prior Publication Data

US 2005/0238133 A1    Oct. 27, 2005

(30) Foreign Application Priority Data

Aug. 14, 2002 (EP) .................. 02078359

(51) Int. Cl.
*A61B 6/03* (2006.01)
(52) U.S. Cl. .............. 378/4; 378/15; 378/901
(58) Field of Classification Search ............. 378/4, 378/8, 15, 22, 901
See application file for complete search history.

(56) References Cited

U.S. PATENT DOCUMENTS

| | | | |
|---|---|---|---|
| 4,590,558 A | 5/1986 | Glover et al. | |
| 4,709,333 A | 11/1987 | Crawford | |
| 5,243,664 A | 9/1993 | Tuy | |
| 5,438,602 A | 8/1995 | Crawford et al. | |
| 5,561,695 A | 10/1996 | Hu | |
| 6,018,561 A | 1/2000 | Tam | |
| 6,094,467 A | 7/2000 | Gayer | |
| 6,125,193 A | 9/2000 | Han | |
| 6,721,387 B1 * | 4/2004 | Naidu et al. | 378/4 |
| 2004/0146136 A1 * | 7/2004 | Gringauz et al. | 378/4 |

* cited by examiner

*Primary Examiner*—Edward J. Glick
*Assistant Examiner*—Chih-Cheng Glen Kao

(57) ABSTRACT

A method is disclosed for generating images of a human or animal body on the basis of 3D-reconstructions from 3D-XRAY or 3D-Computer Tomography measurements, which bodies comprise both natural tissue and one or more high-density objects. The method comprises the steps of executing the measurements, distinguishing the one or more high-density objects and executing a separating procedure thereon for generating an improved image of regions of the natural tissue. In particular, the method comprises the following steps: applying a ramp filter on the various projection measurements to single out the one or more high-density objects; segmenting the singled-out one or more high-density objects into a separate 3D reconstruction; suppressing the reconstructed one or more high-density objects from the original projection measurements; and segmenting said projection measurements without the suppressed one or more high-density objects.

5 Claims, 3 Drawing Sheets

METHOD AND APPARATUS FOR GENERATING AN IMPROVED IMAGE OF NATURAL TISSUE IN RECONSTRUCTING BODY IMAGES FROM 3D-MEASUREMENTS

BACKGROUND OF THE INVENTION

The invention relates to an apparatus for generating images of human or animal bodies on the basis of 3D-reconstructions from 3D-XRAY or 3D-Computer Tomography measurements, which bodies comprise both natural tissue and one or more high-density objects. A principal category of such objects is represented by intentionally introduced objects for maintaining or improving the quality of human or animal life, such as objects being in the form of surgical implants made from metal or other substances, reconstruction screws, plugs filled into teeth, coils introduced into blood vessels, and various others. A secondary category is without limitation formed by high-density markers used for allowing a registration to match various different data sets. The 3D reconstructing methods recited supra, and possibly others as well, are suffering from the visual artifacts that such high density objects may cause in their neighbourhood, and which artifacts will lessen the quality of the eventual image, and thereby diminish its value for diagnostic, curative and other purposes. In consequence, it would be advantageous to have an approach for suppressing such artifacts. The inventors have recognized the advantage of suppressing the high-density object(s) from the processing in an early stage of the latter.

SUMMARY TO THE INVENTION

In consequence, amongst other things, it is an object of the present invention to provide an image generating method that does not suffer from the above artifacts from the high-density bodies introduced.

A further object of the present invention is to supplement the image from the natural tissue in a secondary processing stage with the image of such high density object(s) whilst still avoiding the generation of the above artifacts.

By itself, U.S. Pat. No. 4,590,558 discloses a method for removing objects from CT images, wherein an operator defines a "rub-out" region that encompasses the object to be removed, whereafter the rub-out region is subjected to an averaging function. The operations by the operator clearly necessitate appreciable effort by a skilled worker who must carefully consider the possible location and shape of the high-density object, and on the basis thereof set the rub-out region. The prior art approach will nevertheless be prone to human and other errors, and an automatic procedure would therefore be much preferred.

Furthermore, U.S. Pat. No. 6,094,467 requires, next to the standard imaging apparatus an additional hardware facility with many narrow-beam detection facilities for determining the extent, and in particular, the boundaries of high attenuation objects and for thereby reducing the artifacts that the high attenuation objects would cause, without removing the high attenuation objects from the image. The additional plurality of narrow beam detection facilities represent additional cost and additional control operations, and in consequence, the present inventors have undertaken to derive all necessary information from a single measuring system.

The invention also relates to a method being arranged for implementing the apparatus, and to a computer program and to a computer program product comprising instructions for controlling hardware for thereby being arranged for implementing the method. Further advantageous aspects of the invention are recited.

BRIEF DESCRIPTION OF THE DRAWING

These and further aspects and advantages of the invention will be discussed more in detail hereinafter with reference to the disclosure of preferred embodiments, and in particular with reference to the appended Figures that show.

DETAILED DESCRIPTION OF PREFERRED EMBODIMENTS

Figure 1:
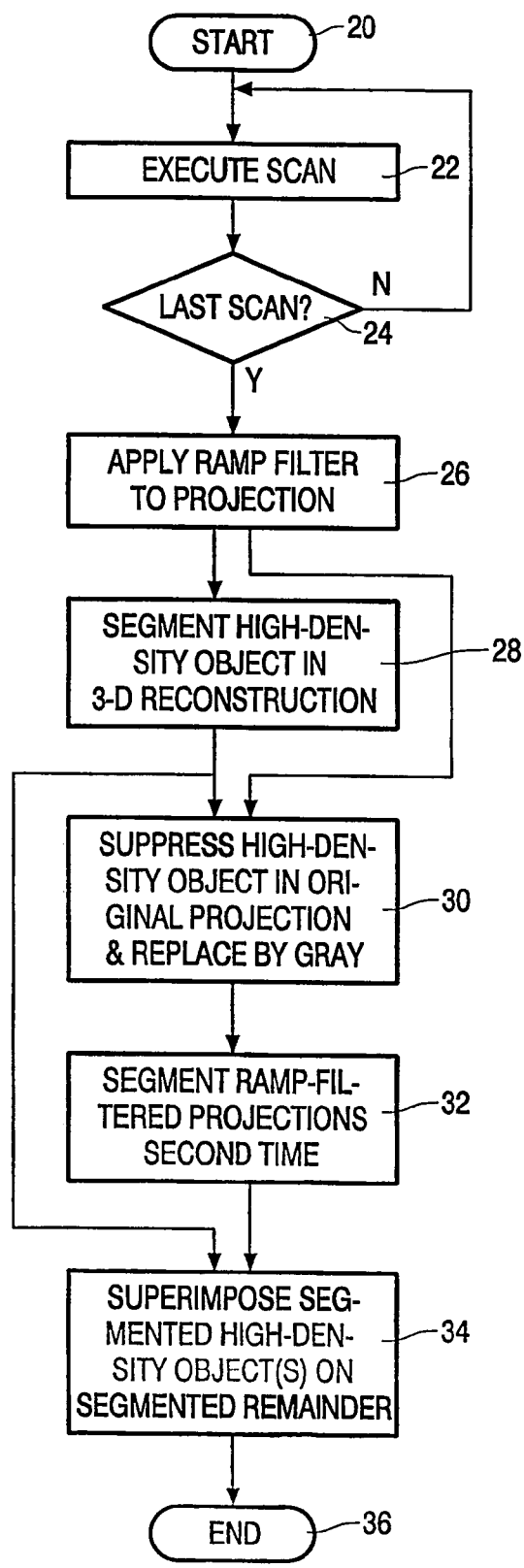
FIG. 1, a flow diagram of a procedure according to the present invention.

FIG. 1 illustrates a flow diagram of a procedure according to the present invention. In block 20, the procedure is started and the necessary hardware and software facilities are assigned. In block 22 the measuring apparatus executes a measuring scan. The prime considered technology is 3D-XRAY (3D-RX), but 3D-CT (computer tomography) technology could be enhanced as well. In block 24, the system determines whether all intended scans have been executed. If no, the next scan is made after an appropriate rotation of the apparatus; if yes, the procedure proceeds to block 26. In block 26, a ramp filter in the direction of rotation is applied to the projection. The setting of the ramp may be done once and for all, it may be done on the basis of statistical processing, such as based on the assumption that the area covered by the high density object(s) is generally small, or it may be done in a heuristic or even intuitive manner, or it could be effected by an operator person. Inasmuch as the high-density objects would generally cause a much greater attenuation that the tissues, the precise setting of the discrimination threshold is not critical.

Next, in block 28, the filtered out high-density object(s) are segmented to get a 3D reconstruction thereof. Next, in block 30 the high-density objects are suppressed in the original projection. Advantageously, they are then replaced by one or more gray values. This may be done by linear interpolation between the neighbouring pixels, by replacing each suppressed object by a single standard value, or by some other appropriate steps. In block 32, the ramp-filtered projections are then segmented a second time, but now without the high-density object(s). A straightforward approach would be to use exactly the same discrimination threshold as for the input values to block 28.

Finally, in block 34, the segmented one or more high-density objects from block 28 are superimposed on the segmentation result of the remainder. Finally, in block 36, the procedure is terminated, and the assigned facilities are relinquished again. The flow chart represents in various respects a simplification. For example, no escape procedure has been shown other than at the successful termination of the processing. Further, a trial and error procedure could be used for effectively setting the ramp threshold.

Figure 2:
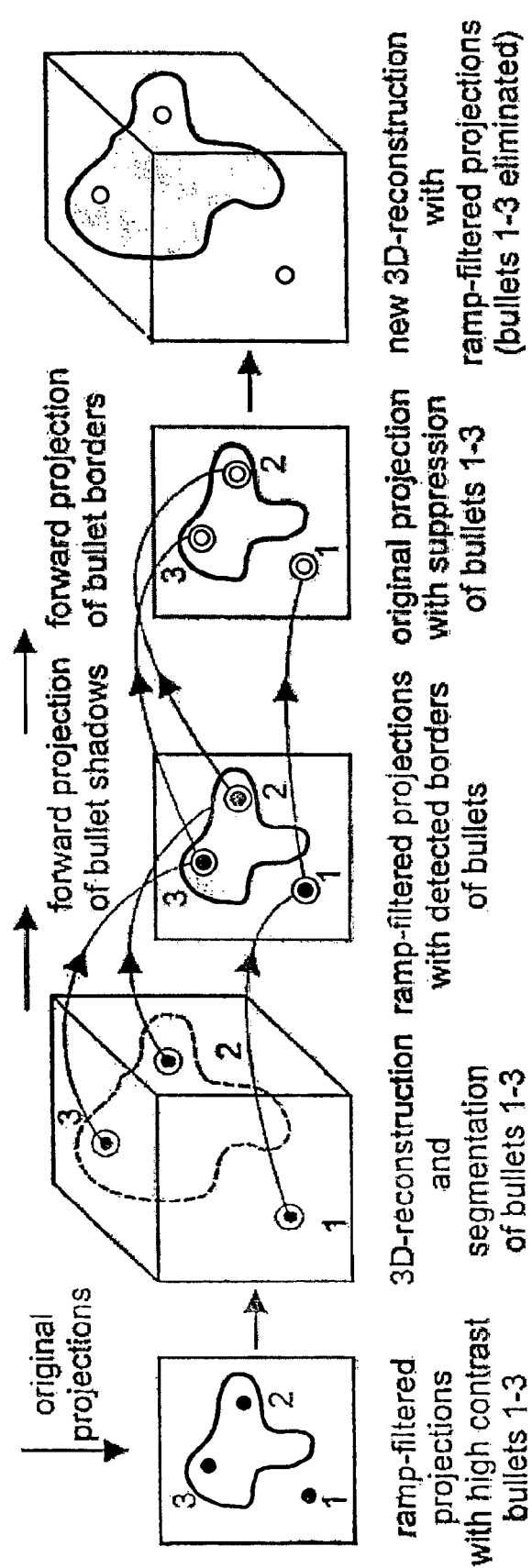
FIGS. 2a–2e, the principle of suppression of the high-density objects.

FIGS. 2a–2e, illustrate the principle of suppression of the high density objects. The method will be described for 3D-RX. A 3D-imaging modality bases on a number of projections acquired during a rotational run with a motorized C-arm system. FIG. 2a shows one simplified projection image. Therein, items 1 to 3 are high-density objects or so-called bullets used for registration of different data sets. After registration, the bullets must be eliminated for a 3D-reconstruction in order to avoid artifacts. When measuring an intensity curve across the projection, at the position of the bullet a signal of high-intensity arises. This signal has to be suppressed and may be filled with gray values derived from the neighbourhood that comprises surrounding structures with lower densities.

The suppression of the high-density object(s) is effected by using ramp-filtered projections, which at the same time improves and simplifies the reconstruction. In this respect, FIG. 2a shows a projection image with bullets 1, 2, 3 clearly visible in the form of black circles. In a first processing step, all projections are ramp-filtered and used for a 3D-reconstruction through back-projection with the well-known Feldkamp algorithm. Also, the bullets, or for that matter, other high-density objects, are segmented in the 3D-reconstruction, resulting in the picture of FIG. 2b. The ramp-filtering results in sharper edges of the bullets, and the 3D-reconstruction enhances the contrast. Through so acting, the segmentation of the high-density objects from the surrounding tissue or structures of their neighbourhood can be effected much better. Next, the bullets can be discriminated by a simple threshold, so that in consequence only the bullets themselves are visible in the form of points with encircling rings. The latter represent the shadow of the bullet in question.

Now, in a third processing step, the remaining bullets are forward projected into ramp-filtered versions of the original projections in order to mark the search regions for the respective bullet borders, leading to the result illustrated in FIG. 2c. After the above processing, the detected borders of the bullets will be forward projected into the original projections, resulting in the image shown in FIG. 2d. In the fourth processing step, the bullets are suppressed by substituting them by the gray values of the structures in their surrounding neighbourhood, such as by linear interpolation between the respective entry point and the corresponding exit point of the bullet in question. Subsequently, a new 3D-reconstruction is performed through again applying the Feldkamp algorithm with ramp-filtered projections. Thereby, the bullets are reduced or even eliminated, such also including removal of the artifacts caused by the bullets, leading to the image shown in FIG. 2e.

Figure 3:
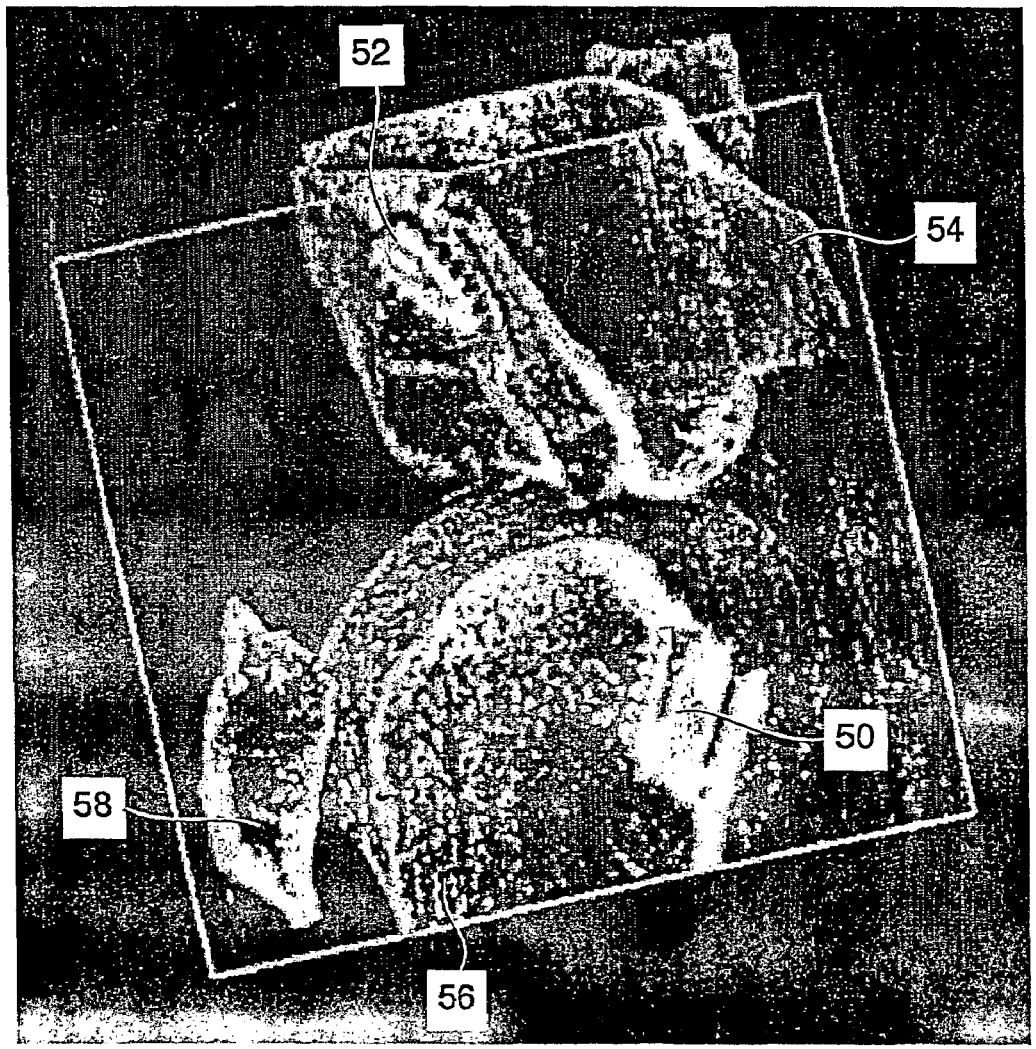
FIG. 3, a 3D reconstruction image of metallic screws in a human knee environment, executed whilst including the suppression and superimposing method for high-density objects according to the present invention.

FIG. 3 illustrates a 3D reconstruction image of metallic screws in a human knee environment, executed whilst including the suppression and superimposing method for high-density objects according to the present invention. The reconstruction clearly shows the knee joint made up of two major bones and the knee-cap, and also two screws used for clinically fixating bone parts to each other. Furthermore, clearly, no artifacts can be seen in the image. The result is attained through including the high-density suppression method in the 3D-reconstruction. The final image is reconstructed by matching the 3D-data set of the bone structures with the 3D-reconstruction of the segmented screws. Furthermore, the gray values of the screws has been adapted to show both screws and bones at the same time. Such adapting may be represented by reducing the overall dynamic representation of the various objects, and in particular, of the high-density objects. Such simultaneous presentation allows a better diagnosis of the region between the screws and the surrounding bone structures. Artifacts caused by the high-density implants can be much reduced now.

The inventors have found that the results according to the present invention are much better when using ramp-filtered projections in combination with a 3D-reconstruction like through the Feldkamp algorithm. The edges of the high density bodies will generally be much sharper and the contrast is improved. Thereby, a segmentation of the implants from the surrounding structures can be done much better. The segmentation can be easily performed with a simple threshold. This is an important aspect of the present invention, inasmuch as segmentation algorithms are often quite complex and thereby, time-consuming.

What is claim is:

1. An apparatus for generating images of a subject on the basis of 3D-reconstructions from 3D-XRAY or 3D-Computer Tomography measurements, which subject comprises both natural tissue and one or more high-density objects, said apparatus comprising a measuring facility for executing said measurements, a distinguishing facility for distinguishing said one or more high-density objects and executing a separating procedure thereon for generating an image of regions of said natural tissue, said apparatus being characterized by comprising:
a ramp-filtering facility for applying a ramp filter in the direction of rotation to various projection measurements and a back-projecting facility fed by said ramp-filtering facility for back-projecting the various filtered projections into a 3D-volume reconstruction;
a segmenting facility fed by said back-projecting facility for segmenting in said 3D-volume reconstruction said one or more high-density objects by a thresholding procedure and a forward projecting facility fed by said segmenting facility for executing a forward projection of a shadow(s) of the segmented one or more high-density objects onto the ramp-filtered projection, whilst marking borders of said one or more high-density objects in the ramp-filtered projections;
a suppressing facility fed by said forward projecting facility for suppressing the reconstructed one or more high-density objects from the original projection measurements and said suppressing facility is operative for executing an appropriate substitution of gray values derived from a physical neighbourhood of said one or more high-density objects instead of said one or more high-density objects in question;
and a retro-coupling facility fed by said suppressing facility for executing a back-projection of the various filtered projections with corrected profiles through exclusion of the suppressed one or more high-density objects and outputting a reconstruction result.

2. An apparatus as claimed in claim 1, and furthermore comprising a superimposing facility fed by said forward projecting facility for receiving said one or more high-density objects for superimposing thereof onto said reconstruction result.

3. An apparatus as claimed in claim 1, and furthermore comprising adapting means for relatively adapting the gray values of said one or more high-density objects and said natural tissue in a predetermined gray value range to show both of said one or more highdensity objects and said natural tissue at same time.

4. A method of generating images of a human or animal body on the basis of 3D-reconstructions from 3D-XRAY or 3D-Computer Tomography measurements, which body comprises both natural tissue and one or more high-density objects, said method comprising the steps of executing said measurements, distinguishing said one or more high-density objects and executing a separating procedure thereon for generating an improved image of regions of said natural tissue, said method being characterized by comprising the steps of:

applying a ramp filter in the direction of rotation to various projection measurements and back-projecting the various filtered projections into a 3D-volume reconstruction;

in said 3D-volume reconstruction, segmenting said one or more high-density objects by a thresholding procedure and executing a forward projection of a shadow(s) of the segmented one or more high-density objects onto the ramp-filtered projection, whilst marking borders of said one or more high density objects in the ramp-filtered projections;

suppressing the reconstructed one or more high-density objects from the original projection measurements whilst executing an appropriate substitution of gray values derived from a physical neighbourhood of said one or more high-density objects instead of said one or more high-density objects in question;

and secondarily executing a back-projection of the various filtered projections with corrected profiles and thereby without the suppressed one or more high-density objects.

5. A computer readable medium containing instructions for controlling a computer system to perform the steps of a method of generating images of a subject on the basis of 3D-reconstructions from 3D-XRAY or 3D-Computer Tomography measurements, which subject comprises both natural tissue and one or more high-density objects, said method comprising the steps of executing said measurements, distinguishing said one or more high-density objects and executing a separating procedure thereon for generating an improved image of regions of said natural tissue, said method furher comprising the steps of:

applying a ramp filter in the direction of rotation to various projection measurements and back-projecting the various filtered projections into a 3D-volume reconstruction, in said 3D-volume reconstruction, segmenting said one or more high-density objects by a thresholding procedure and executing a forward projection of a shadow(s) of the segmented one or more high-density objects onto the ramp-filtered projection, whilst marking borders of said one or more high density objects in the ramp-filtered projections;

suppressing the reconstructed one or more high-density objects from the original projection measurements whilst executing an appropriate substitution of gray values derived from a physical neighbourhood of said one or more high-density objects instead of said one or more high-density objects in question;

and secondarily executing a back-projection of the various filtered projections with corrected profiles and thereby without the suppressed one or more high density objects.

* * * * *